United States Patent [19]
Day et al.

[11] Patent Number: 5,174,475
[45] Date of Patent: Dec. 29, 1992

[54] SEQUENTIAL DOSING OF ANTIFUNGAL AND ANTIINFLAMMATORY COMPOSITIONS

[75] Inventors: Robert M. Day, Durham; Charles E. Holland; George E. Van Lear, both of Chapel Hill, all of N.C.

[73] Assignee: Glaxo Inc., Research Triangle Park, N.C.

[21] Appl. No.: 675,207

[22] Filed: Mar. 26, 1991

[51] Int. Cl.⁵ ............................................. B67D 5/60
[52] U.S. Cl. ................................ 222/144.5; 222/94; 222/135; 514/179; 514/867
[58] Field of Search ..................... 222/94, 144.5, 135

[56] References Cited

U.S. PATENT DOCUMENTS 4,298,604 1/1981 Hammell et al. ............... 424/243
4,548,606 10/1985 Larkin ............................. 604/414
4,838,457 6/1989 Swahl et al. ..................... 222/48
4,993,594 2/1991 Becker et al. ................... 222/48

OTHER PUBLICATIONS

PDR, 45th Edition, (1991), pp. 2004.
Pariser, Postgraduate Medicine, vol. 87, No. 6 (May 1, 1990), pp. 101–108.

Primary Examiner—Leonard Schenkman
Attorney, Agent, or Firm—David J. Levy

[57] ABSTRACT

A sequential dosing medicament for topical treatment of fungal infections comprising a first pharmaceutical composition having an antifungal agent and an antiinflammatory agent, e.g. a steroid, a second separate pharmaceutical composition having only an antifungal agent as the active ingtredient. Also a method for such sequential dosing, particularly using oxiconazole as the antifungal agent and fluticasone as the steroid.

7 Claims, 5 Drawing Sheets

SEQUENTIAL DOSING OF ANTIFUNGAL AND ANTIINFLAMMATORY COMPOSITIONS

BACKGROUND OF THE INVENTION

An antifungal/steroid combination pharmaceutical composition is known in the art as seen in U.S. Pat. No. 4,298,604. This composition is designed for topical use for a variety of dermal and vaginal infections such as tinea pedis, tinea cruris and tinea corporis due to, for example, *Trichophyton rubrum, Trichophyton mentagrophytes, Epidermophyton floccosum,* and *Microsporum canis*; candidiasis due to *Candida albicans*; and tinea versicolor due to *Malassezia furfur*. The compositions of the '604 patent are stated to be useful when these infections are accompanied by moderate to severe inflammation. Depending on the severity of the infection, the compositions may be administered one or more times per day for a period ranging from a few days to several weeks until sufficient improvement is obtained, depending upon the judgment of the attending clinician. The compositions may be administered topically in the form of creams, ointments, lotions, solutions, aerosol sprays, and the like. Although an ointment is likely to be the most effective vehicle, because of the occlusive effect of the anhydrous petrolatum vehicle, a cream or lotion is likely to be more esthetically acceptable to the patient. For vaginal administration, the use of tablets, suppositories or coated condoms may also be advantageous.

A particular antifungal/steroid combination topical composition, i.e. one containing both antifungal and steroid pharmaceutical active ingredients, is the Lotrisone® brand of clotrimazole and betamethasone dipropionate cream, USP.

The U.S. Food and Drug Administration (FDA) published guidelines in 1984 for the conduct of clinical studies, and thus by implication for the regimens to be in approved labeling, for antifungal therapy. In the treatment of infections such as tinea cruris, if the condition persists after 2 weeks, treatment with the particular pharmaceutical composition should be discontinued. This would indicate a failure of that particular therapy and the need to institute an alternative therapy. In the case of an antifungal/steroid treatment, such failure may be due to the steroid causing the development of i) local immune suppression, thus blocking the body's ability to fight the infection, ii) an increase in the growth rate of the fungus and/or iii) tolerance, where the steroid is thought to decrease the efficacy of the combination. Thus, the 45th Edition of the Physicians Desk Reference Medical Economics Company, Oradell, N.J. (1991) at page 2004 states that "Treatment with Lotrisone Cream should be discontinued if the condition persists after two weeks in tinea cruris and tinea corporis, and after four weeks in tinea pedis. Alternate therapy may then be instituted with Lotrimin Cream, a product containing an antifungal only." This is the switching from one therapy to another based on failure of the first therapy.

In the article "Cutaneous candidiasis" by David M. Pariser at pages 101-108 of Postgraduate Medicine, Vol. 87, No. 6 (May 1, 1990), the author states that dermatologists have advocated the addition of a corticosteroid to an antifungal preparation and that after 5 to 7 days of treatment, the antifungal agent may be used alone.

An object of the present invention is a pharmaceutical preparation, particularly a device, which operates to first dispense an antifungal/antiinflammatory, e.g. an antifungal/steroid, topical preparation according to a regimen which follows automatically with an antifungal alone.

A further object of the present invention is a unitary therapy for the treatment of a topical fungal infection with oxiconazole and an antiinflammatory agent such as fluticasone followed by oxiconazole alone.

SUMMARY OF THE INVENTION

A topical medicament adapted for multiple dosing wherein a first composition having both an antifungal and an antiinflammatory is dispensed first followed by the dispensing of a second composition having only an antifungal as the active ingredient. Preferably, the antifungal is oxiconazole and the antiinflammatory agent is fluticasone. The medicament is preferably in the form of a dispenser which has a single activation means whereby the initial activations dispense the first composition and subsequent activations dispense the second composition.

DETAILED DESCRIPTION OF THE INVENTION

Figure 1:
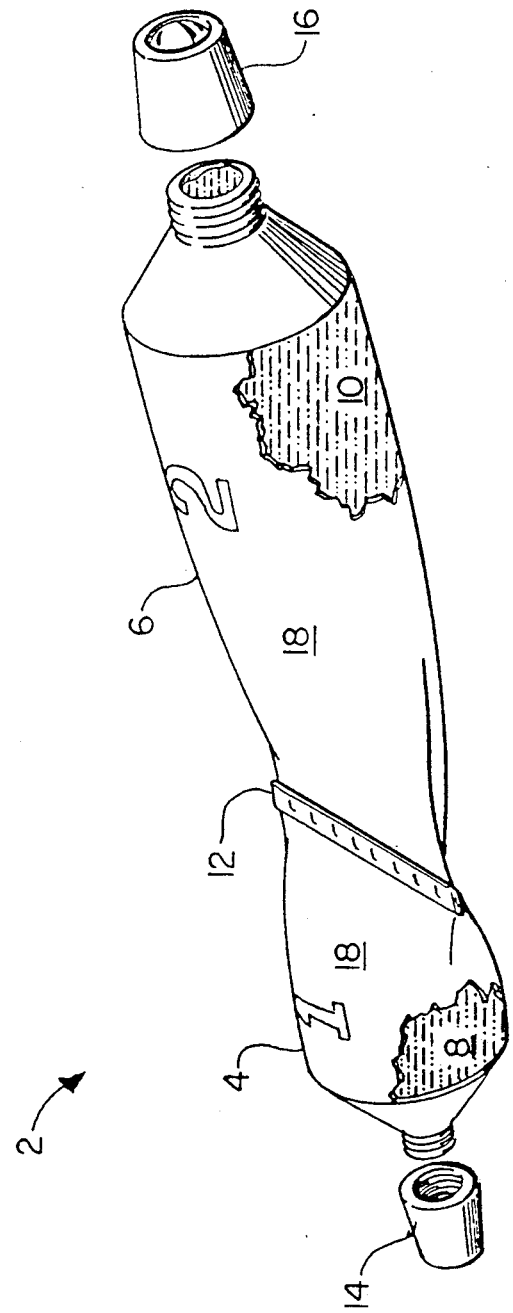
FIG. 1 depicts a 2-compartment tube with two exit nozzles for the first and second compositions of the invention.

The multiple dosage topical medicament container of the invention comprises a first pharmaceutical composition comprising an antifungal agent and an antiinflammatory, e.g. a steroid, and a separate second pharmaceutical composition consisting essentially of an antifungal agent. The antifungal agent is preferably the same in both compositions and is a topically-effective antifungal agent with examples being the following and oxiconazole being a particular example:

1. imidazoles e.g., oxiconazole, clotrimazole, miconazole, sulconazole, ketoconazole.
2. allylamines e.g., naftifine, terbinafine
3. triazoles e.g., fluconazole, itraconazole
4. glucan synthase inhibitors e.g., cilofungin
5. chitin synthase inhibitors e.g., nikkomycin Z
6. polyenes e.g., amphotericin B, nystatin, faeriefungin
7. griseofulvin
8. morpholine derivatives e.g., amorolfine
9. pyridones, pyridines or pyridinones e.g., ciclopirox olamine
10. triazines e.g., pyrido[3,4-e]-1,2,4-triazines
11. pyrimidines e.g., flucytosine Oxiconazole is the approved name for 1-(2-(4-chlorophenyl)-2-[(2,4-dichlorophenyl)methoxyimino)ethyl)-1H-imidazole and is described in U.S. Pat. Nos. 4,124,767, 4,443,612 and 4,550,175. Suitable physiologically acceptable salts of oxiconazole include the hydrochloride, sulphate and nitrate salts. Preferably oxiconazole will be in the form of its nitrate.

Antiinflammatory agents for use in the present invention include one or more of the following types which reduce burning, swelling, redness, itching or pain:
1. glucocorticosteroids
2. 5-lipoxygenase inhibitors e.g., Ionapolene, DuP 654
3. lipoxygenase/cyclooxygenase inhibitors e.g., benoxaprofen, tepoxalin, BI-L-93BS
4. phospholipase A2 inhibitors e.g., manoalide
5. phospholipase C inhibitors
6. protein kinase C inhibitors, e.g. sphingosines
7. interleukin-1 inhibitors e.g., IX-207-887
8. interleukin-1 receptor antagonists e.g., Synergen's compound
9. 12-HETE inhibitors, e.g. DuP 630 and DuP 983
10. retinoids e.g., CD271
11. PAF antagonists e.g., BN-50730, PCA-4248
12. essential fatty acids and their analogs e.g., CD554, CD581
13. beta-2 agonists e.g., salmeterol
14. antipruritics In particular, glucocorticosteroids, also known by the term corticosteroids or simply steroids, are used in the present invention. The effects of corticosteroids are described in detail by W. Raab in Dermatologica 152 (Suppl. 1) 67–79 (1976).

A steroid for use in the first topical pharmaceutical composition, without being present in the second composition may be any of the medium potency type, such as fluticasone. Fluticasone may be used as the propionate derivative.

Fluticasone propionate is the approved name for s-fluoromethyl 6a,9a-difluoro-11b-hydroxy-16a-methyl-17a-propionyloxy-3-oxandrosta-1,4-diene 17b-carbothioate, which is disclosed in United Kingdom Patent Specification No. 2088877. Fluticasone propionate is a corticosteroid having topical antiinflammatory action. Another name for fluticasone is 6,9-difluoro-11-hydroxy-16-methyl-3-oxo-17-(1-oxopropoxy)-androsta-1,4-diene-17-carbothioic acid, (6a, 11b, 16a, 17a)-S-fluoromethyl)ester.

Concentrations of the antifungal and antiinflammatory active ingredients in the compositions used in the present invention will vary according to the potency of the individuals agents and the severity of the condition being treated. Thus, the antifungal agent may be present in a topical form such as a cream, ointment or lotion in a concentration of about 0.01 to 20.0% on a weight-to-weight basis, in particular about 0.05 to 5.0%. For oxiconazole, a range of about 0.01 to 10% is suitable, preferably 1%. The antiinflammatory may be present in an amount of about 0.0001 to 20.0%, in particular about 0.001 to 10.0%. For a steroid such as fluticasone, an amount of about 0.0005 to 1% preferably 0.05% may be used.

Conditions to be treated according to the present invention include tinea pedis, tinea cruris, tinea corporis, candidiasis, seborrheic dermatitis and tinea versicolor.

The regimen for the particular conditions to be treated according to the present invention is about 7 days for the first composition and 1 to 4 weeks immediately thereafter for the second composition until effective treatment of the particular condition is realized.

Application of the first or second composition may be 1 to 4 times per day.

Compositions according to the invention can conveniently be formulated in conventional manner using one or more pharmaceutically acceptable carriers or excipients. Such compositions may take the form of, for example, ointments, lotions, creams, powders, drops (e.g. eye or ear drops) or sprays. Preferably the compositions of the invention will be in the form of ointments or creams.

Ointments may normally be prepared by melting with soft paraffin, (white petrolatum) incorporating any additives e.g. surfactants and solvents, and blending in a slurry of the drug in a minimum quantity of liquid paraffin. The melt is then cooled under controlled conditions and stirred until solidification occurs.

Creams may normally be prepared by combining the oily phase of an ointment as a melt as described above, with suitable oil and water soluble surfactants and an aqueous phase containing the drug and suitable antimicrobal preservatives, homogenizing to form the cream and stirring gently until cool.

Compositions according to the invention will generally contain additional excipients, for example preservatives (such as benzoic acid), emulsifying agents (such as polysorbates, e.g. polysorbate 60), and viscosity enhancing agents (such as cetostearyl alcohol).

Devices for dispensing the first and second topical pharmaceutical compositions of the invention may be in the form of collapsible tubes, rigid tubes, jars, bottles, ampoules, spray dispensers such as aerosol cans, impregnated pads or any other presentation known in the art. Preferably, the device is unitary, i.e. consists of a single container which which cannot be broken apart such as a single tube or molded pair of tubes, whereby the same device and preferably the same dispensing mechanism and aperture are used for both the first and second compositions. Spanish Patent P. 8803996 filed Nov. 18, 1988 describes a container to hold 2 substances such as pharmaceuticals and dispense them at the same time. The following U.S. Patents teach various dispensers which can be used per se in the present invention or which can be modified in accordance with features shown in the present drawings to thereby by useful in the present invention:

| | |
|---|---|
| 4,830,221 | 4,715,518 |
| 4,821,926 | 4,684,044 |
| 4,793,526 | 4,651,904 |
| 4,793,522 | 4,598,843 |
| 4,776,496 | 4,570,829 |
| | 3,946,908 |

A single cylindrical jar provided with a vertical wall along the diameter line to define two compartments may be used to separate and contain the two compositions used in the invention. Two separate devices may be used, i.e. one for each of the first and second compositions. Preferably, a single device is used for both compositions whereby there is a sequential dispensing of the first followed by the second composition from the same device. The sequential dispensing, i.e. the switching from the first to second composition, may be manual or automatic. By a manual operation, the patient or physician would adjust the device, e.g. by a dial, to dispense the first composition and would then readjust the device to dispense the second. Alternatively, the device in a manual operation would be preset to dispense the first composition and would then be manually adjusted to dispense the second composition.

In an automatic operation, the device would dispense the first composition which has been pre-filled to a pre-set amount and automatically upon its exhaustion, the device would only dispense the second composition. In the automatic mode, the patient could be unaware that a different medication was being dispensed after the switch. Alternatively, the device according to the present invention may dispense a preset number of applications of the first composition, i.e. the antifungal/antiinflammatory composition, as opposed to a preset amount of the first composition. It would then switch automatically to the antifungal composition or one would simply be unable to dispense more and would know at that point to use the second composition. In this mode, the device would dispense about 7, 14, 28 or 56 times depending upon whether the first composition was to be dispensed for 7 or 14 days and whether dosing would be four times per day, twice or once. These factors could be programmed into the device at manufacture or by the pharmacist after reading the physician's prescription.

With reference to the drawings, devices for use in the present invention include the tubes, syringes, pumps and other dispensers of the Figures.

FIG. 1 shows a tube 2 having a first compartment 4 and a second compartment 6 for holding first and second compositions 8 and 10, e.g. creams or ointments, which compositions are kept apart by a diaphragm or a crimped or heat-sealed closure 12 as appropriate for the material used. The compositions may be dispensed by removing caps 14 or 16, respectively, which caps are screwed on or which pop up as known in the art, e.g. the toothpaste tube art. After cap 14 or 16 is removed, the sidewalls 18 are pressed inwards to displace composition 8 or 10. As indicated in FIG. 1, cap 14 is a different size than cap 16 to prevent their being attached to the wrong compartment and contaiminating each other.

Figure 2:
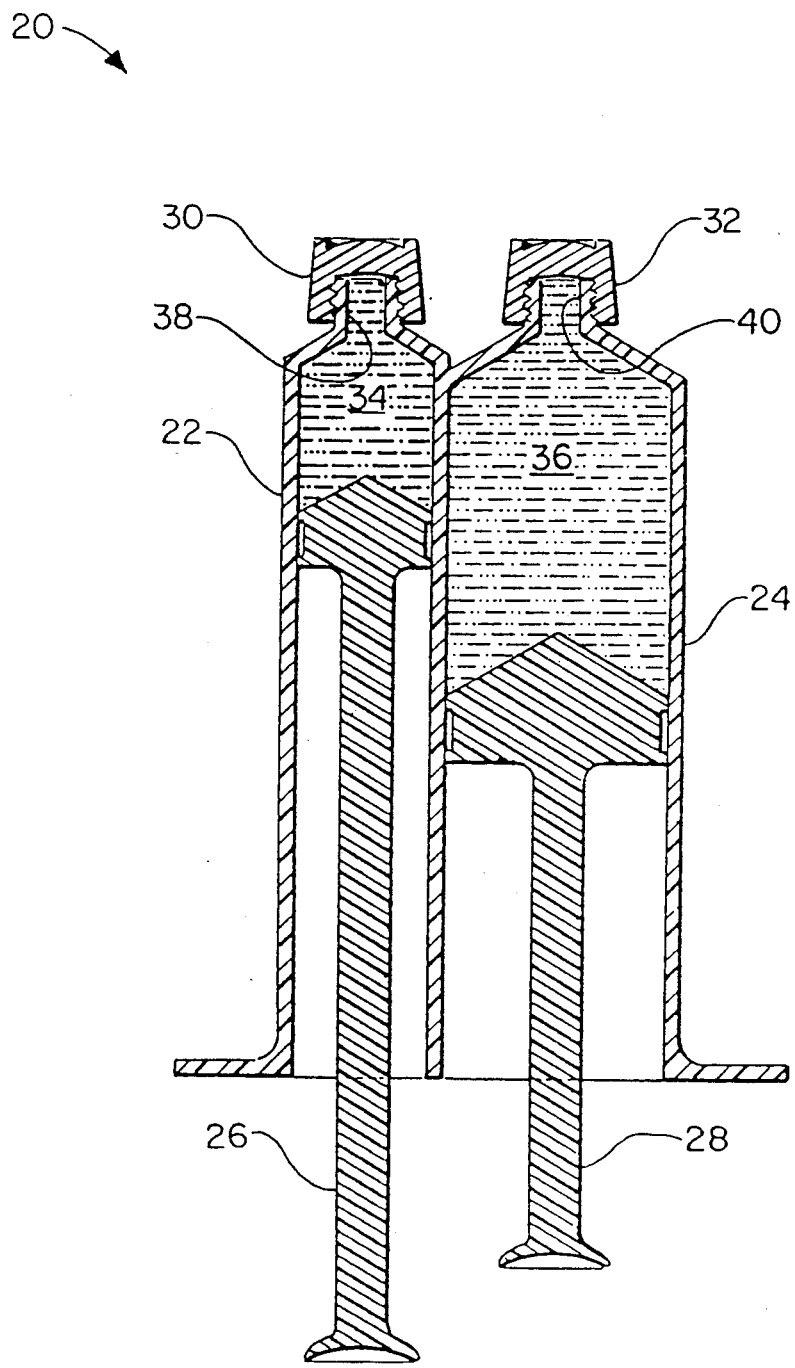
FIGS. 2 and 2a depict a dual syringe type dispensers for the first and second compositions of the invention.
Figure 2A:
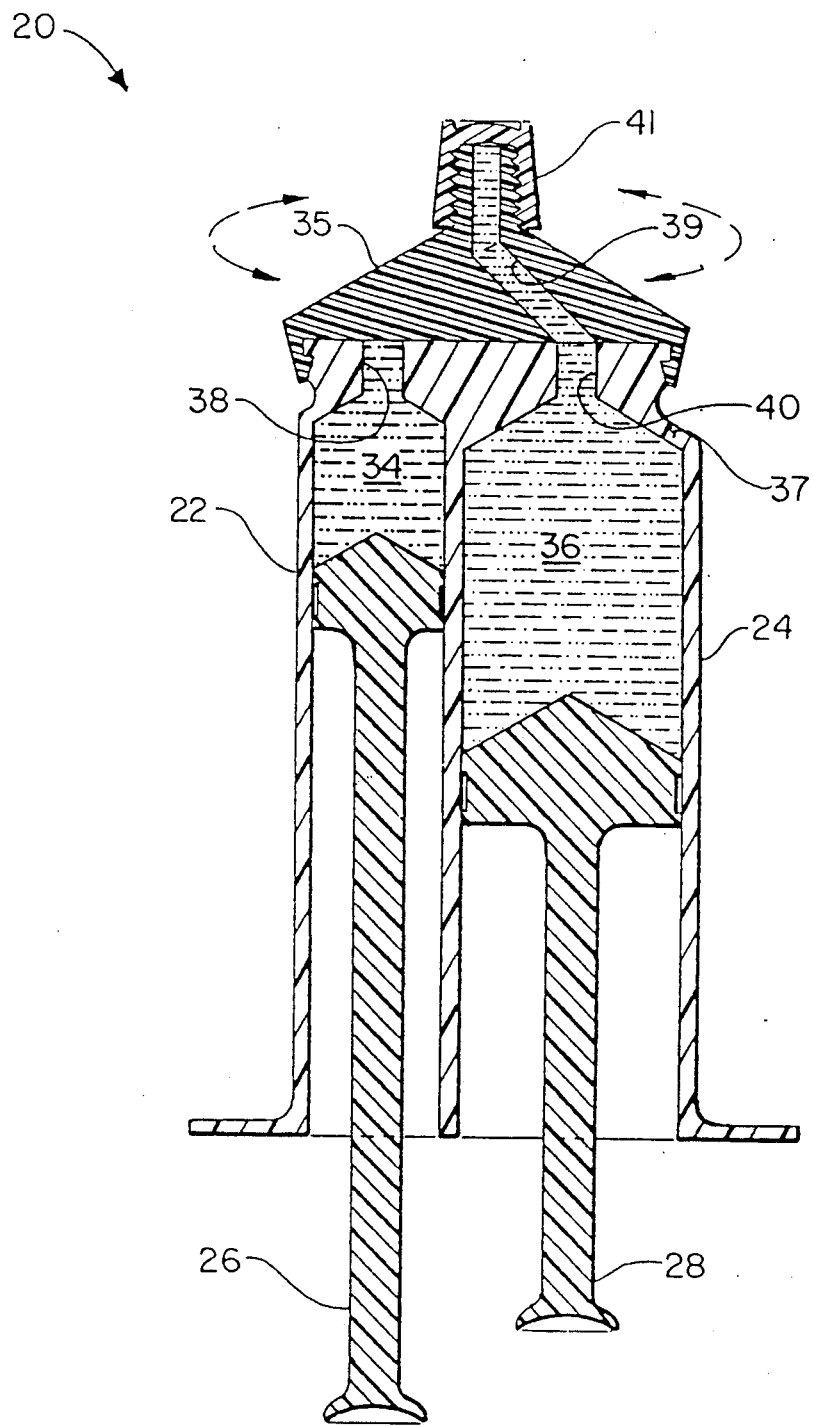

FIG. 2 shows a dual syringe dispenser 20 having cylinders 22 and 24 in which separate plungers 26 and 28 friction fit, e.g by means of a rubber O-ring or other seal. Pressure on either plunger 26 or 28 after removal of caps 30 or 32 from tips 38 or 40, respectively, allows composition 34 or 36, respectively, to exit from the unit and be applied to the skin. In place of individual caps 30 and 32 in FIG. 2, the arrangement shown in FIG. 2a may be used. In FIG. 2a, a permanent cap 35 is fitted over nozzle 37 which has running through it both tip portions 38 and 40 of cylinders 22 and 24. A single passageway 39 is provided through cap 35 for exiting of either composition 34 or 36. A removable cap 41 is also provided to fit over permanent cap 35. Cap 35 may be rotated whereby passageway 39 can either be aligned with tip 38 or 40 depending on which composition is to be dispensed. Indicia would be provided on cap 35 so that the user would know which alignment was being provided for passageway 39, i.e. whether composition 34 or 36 would be dispensed through passageway 39. The arrangement of FIG. 2a would prevent both plungers 26 and 28 from being simultaneously pressed and unintentionally dispensing both compositions 34 and 36. Dual syringes of suitable design are those known in the art of packaging such as the "Sleeve-lok" syringe system available from Bio-Pak Associates of 5018 Industrial Rd., Farmingdale, N.J. 07727. Such systems are commercially available for materials such as 2-part epoxy glues.

Figure 3C:
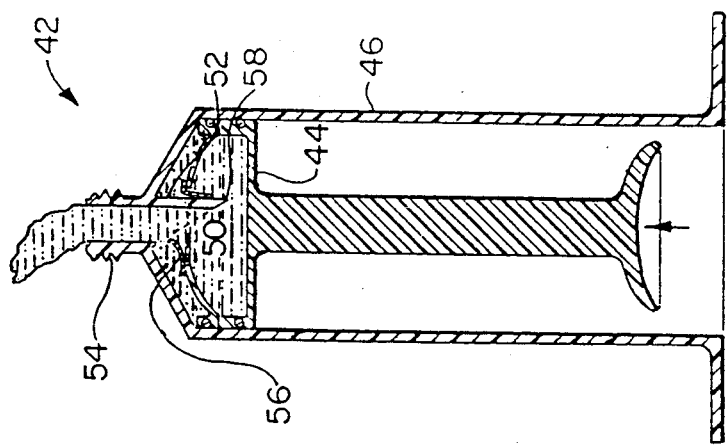
FIGS. 3a, 3b and 3c show a pump dispenser in three stages of use for two compositions separated by a diaphargm in a single cylinder.
Figure 3B:
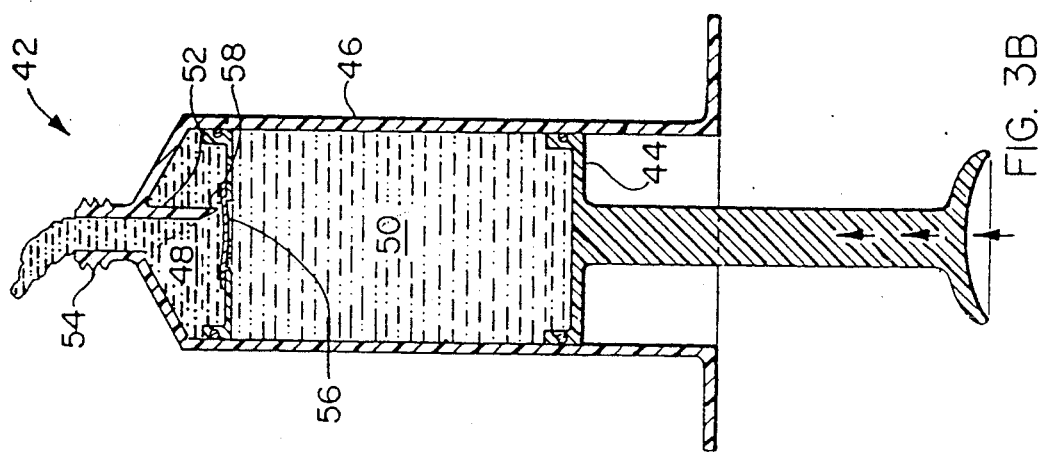
Figure 3A:
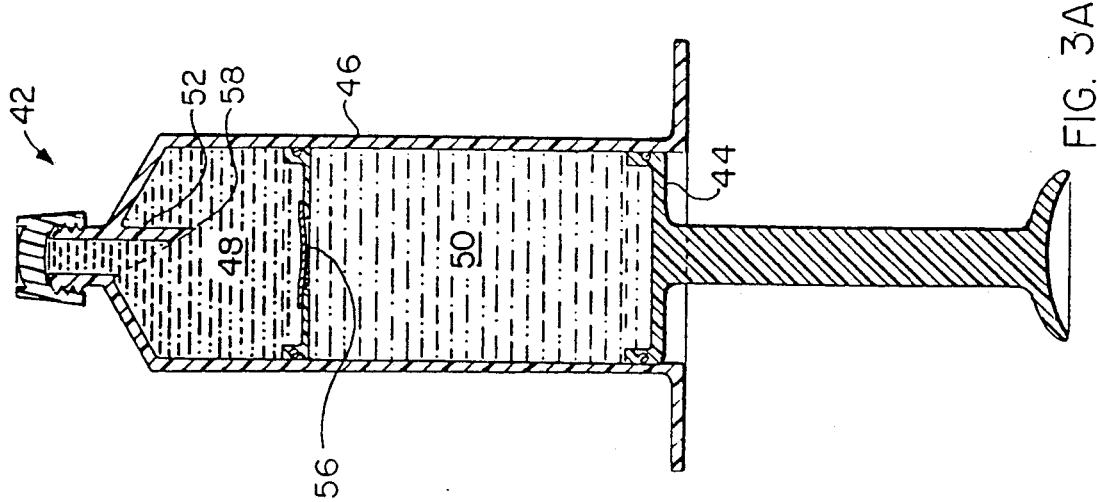

FIGS. 3a, 3b and 3c show a cylindrical pump 42 which may operate by applying pressure to plate 44 or by either the Calmar or Pfeiffer systems known in the toothpaste pump art. Such systems are available from Calmar Inc. of 333 South Turnbull Canyon Rd, City of Industry, Calif. 91749 and Pfeiffer Inc. of 12 Roszel Road, Princeton, N.J. 08540. Calmar pumps are described in U.S. Pat. Nos. 4,598,843, 4,684,044, 4,715,518 and 4,793,522. Pump 42 has a single cylinder 46 containing the first and second compositions, 48 and 50, for use in the present invention. Initially, activation of the pump 42 will result in dispensing of a stream of composition 48 through tube 52 and out nozzle 54 as in FIG. 3b. Movement of both compositions up the cylinder after repeated activations will also push up diaphragm 56 which is deployed to physically separate compositions 48 and 50. The edges of diaphragm 56 and those of plate 44 contact the inside surface of cylinder 46 as a tight seal to ensure that as the diaphragm 56 and plate 44 move up the cylinder, the two compositions do not mix and are not left behind in cylinder 46 after passage of plate 44. When nearly all of the first composition 48 has been dispensed, diaphragm 56 will come into contact with the sharp edge 58 of tube 52. Further pressure by activation of the unit will cause the edge 58 to pierce the diaphragm 56 as in FIG. 3c whereby the subsequent activations will cause the second composition 50 to exit the unit through tube 52 and nozzle 54. Pump mechanisms as well as their nozzle and cylinder configurations are well described in the art as depicted in U.S. Pat. Nos. 4,220,261 and 4,961,520.

Figures 4, 4A:
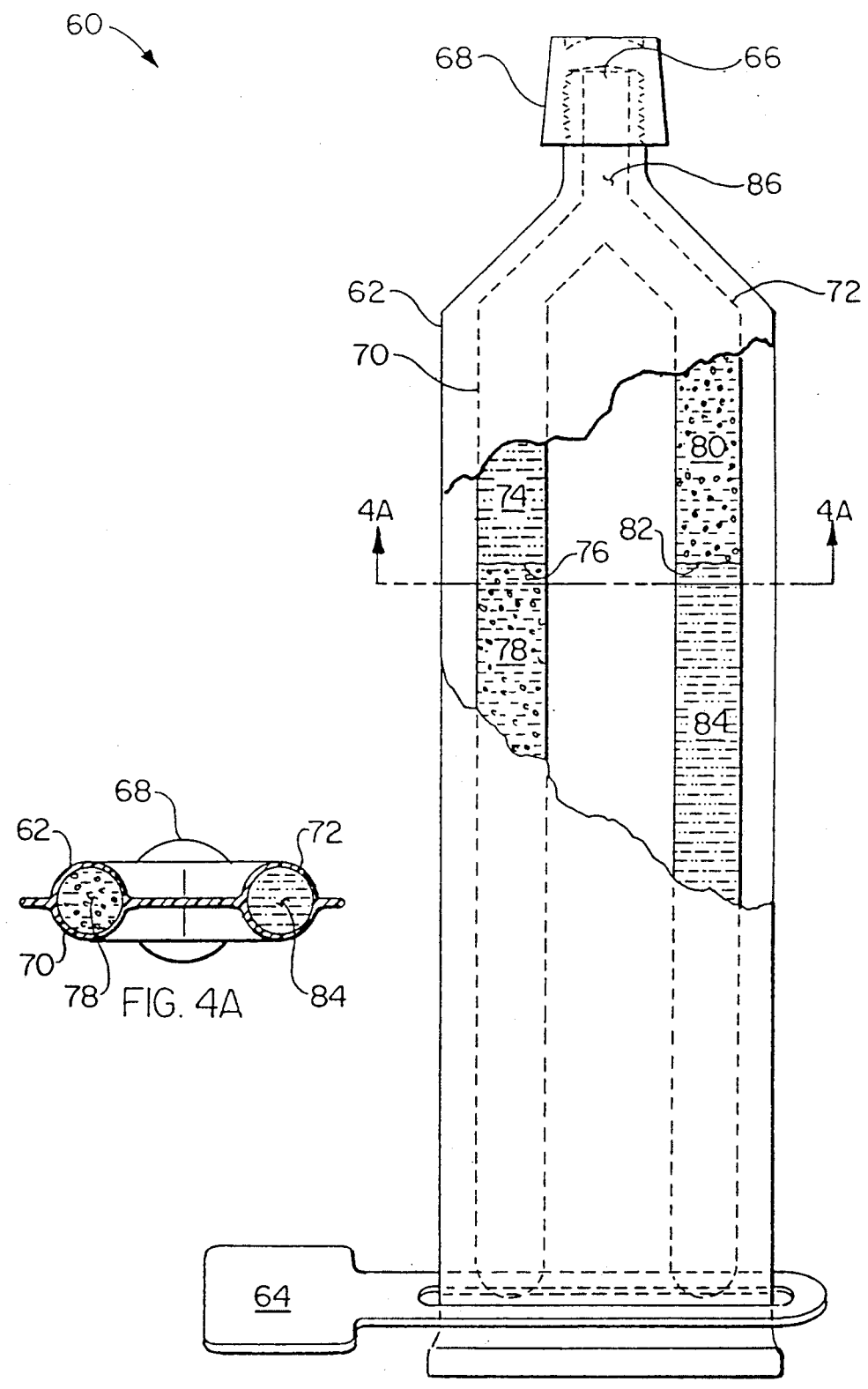
FIG. 4 shows a dual bladder squeeze tube for dispensing two compositions simultaneously where an active ingredient(s) is only in one of the two compositions being dispensed at any one time.
FIG. 4a shows a cross-section of the tube.

FIG. 4 shows a dual bladder dispenser 60 for use in the present invention. FIG. 4a is a horizontal cross-section through bladder tube 60. The dispenser 60 comprises a tube 62 made of a flexible plastic or metal foil material such as is used in toothpaste tubes. A key 64 is provided to be turned whereby the interior contents of tube 62 are made to exit through nozzle 66 after cap 68 is removed. The interior of tube 62 comprises two bladders 70 and 72 the contents of which are each dispensed through nozzle 66 as the key 64 is rotated. The contents of bladders 70 and 72 are each comprised of an inert portion and a portion containing active ingredient(s). Thus, bladder 70 is filled with composition 74 containing a mixture of an antifungal agent and an antiinflammatory agent in a cream or ointment inert base. Below a dividing line 76, the bladder 70 is filled with a composition 78 consisting only of an inert base, preferably the same base as is used in composition 74. The reverse is true in bladder 72 where composition 80 is an inert base, preferably identical to composition 78. Below the inert base composition 80 is a dividing line 82 below which the bladder 72 is filled with an antifungal composition 84 which consists of an antifungal agent in an inert base. Preferably the base cream or ointment in all 4 compositions 74, 78, 80 and 84 is the same. As the key 64 is turned, compositions 74 and 80 are dispensed through a mixing channel 86 which communicates between bladders 70 and 72 and nozzle 86. When dividing lines 76 and 82 pass through channel 86, the composition being dispensed will change from a mixture of 74 and 80 to a mixture of 78 and 84. Thus, the tube 60 provides a means to dispense sequentially a first pharmaceutical composition containing a mixture of an antifungal agent and an antiinflammatroy agent followed by an antifungal agent above without there being any changeover being recognized by the patient and without the patient being required to be reminded of the need to do so.

Preferably, the dispenser used in the invention will keep the first and second compositions out of physical contact with each other.

Also part of the present invention is a treatment regimen for a topical fungal infection which comprises topically administering said infection with a first pharmaceutical composition comprising an effective amount of oxiconazole an antiinflammatory agent and after a sufficient number of applications for the effects of the antiinflammatory to be manifest, topically administering said infection with a second pharmaceutical composition consisting essentially of an effective amount of oxiconazole.

In the following Examples, a dashed line under an Example letter indicates the same quantity for the particular ingredient as is shown in the first Example letter to the left, e.g. 100 mg of cetostearyl alcohol NF for Example C.

EXAMPLE A

Oxiconazole/fluticasone propionate cream

The following cream may be prepared by mixing the fat phase consisting of the white soft paraffin, cetostearyl alcohol and a portion of the polysorbate 60 in a suitable vessel with stirring at about 80° C. The aqueous phase is prepared by combining water, benzoic acid and propylene glycol with mixing at about 80° C. When both phases are at 80° C., add the fat phase to the aqueous phase with stirring. Cool the cream base to 60° C. The steroid and antifungal agents are slurried in an aqueous polysorbate 60 solution and mixed into the cream base which is allowed to cool to ambient temperature during this process.

| Ingredients | % w/w | For 1 gram (milligrams) |
|---|---|---|
| oxiconazole nitrate | 1.147 | 11.47 |
| fluticasone propionate | 0.05 | 0.5 |
| cetostearyl alcohol NF | 10.0 | 100 |
| white soft paraffin USP | 10.0 | 100 |
| polysorbate 60 NF | 2.5 | 25 |
| propylene glycol USP | 10.0 | 100 |
| benzoic acid USP | 0.2 | 2 |
| purified water USP | 66.103 | 661 |

Excipient materials may vary ± 10%.

EXAMPLES B-F

Oxiconazole/fluticasone propionate cream

The following Examples B-F describe pharmaceutical creams with ingredients being listed in milligrams, which may be prepared in the same manner as Example A.

| Ingredients | B | C | D | E | F |
|---|---|---|---|---|---|
| oxiconazole nitrate | 11.47 | 1.147 | 22.94 | 114.7 | 0.1147 |
| fluticasone propionate | 0.5 | 0.05 | 1.0 | 10 | 0.005 |
| cetostearyl alcohol NF | 100 | — | — | — | — |
| white soft paraffin USP | 100 | — | — | — | — |
| polysorbate 60 NF | 25 | — | — | — | — |
| propylene glycol USP | 100 | — | — | — | — |
| benzoic acid USP | 2 | — | — | — | — |
| purified water USP | to make 1 gram | — | — | — | — |

Excipient materials may vary ± 10%.

EXAMPLES G-K

Oxiconazole/fluticasone propionate lotion

Combination antifungal/steroid lotions may be prepared by combining the following ingredients, with amounts being expressed in milligrams and mixing in a blender. The lotion is prepared in similar phase fashion to the cream as in Example A except more water is used.

| Ingredients | G | H | I | J | K |
|---|---|---|---|---|---|
| oxiconazole nitrate | 11.47 | 1.147 | 22.94 | 114.7 | 0.1147 |
| fluticasone propionate | 0.5 | 0.05 | 1.0 | 10.0 | 0.005 |
| cetostearyl alcohol NF | 50 | — | — | — | — |
| white soft paraffin USP | 50 | — | — | — | — |
| polysorbate 60 NF | 12.5 | — | — | — | — |
| propylene glycol USP | 50 | — | — | — | — |
| benzoic acid USP | 2 | — | — | — | — |
| purified water USP | to make 1 gram | — | — | — | — |

Excipient materials may vary ± 10%.

EXAMPLES L-P

Oxiconazole/fluticasone propionate ointment

The following ointments may be prepared by mixing the following ingredients with amounts being expressed in milligrams. The ointment base is prepared by mixing mineral oil and white petrolatum in a suitable mixing vessel at or above 70° C. The active ingredients are suspended in propylene glycol and added to the ointment base with stirring. The mixture is allowed to cool to ambient temperature with continued mixing.

| Ingredients | L | M | N | O | P |
|---|---|---|---|---|---|
| oxiconazole nitrate | 11.47 | 1.147 | 22.94 | 114.7 | 0.1147 |
| fluticasone propionate | 0.5 | 0.05 | 1.0 | 10.0 | 0.05 |
| propylene glycol USP | 50 | — | — | — | — |
| mineral oil | 50 | — | — | — | — |
| white petrolatum | to make 1 gram | — | — | — | — |

Excipient materials may vary ± 10%.

EXAMPLE Q

Oxiconazole 1% cream

An antifungal cream may be prepared by combining and mixing the following ingredients in a similar fashion as described in Example A.

| Ingredients | % w/w | For 1 gram (milligrams) |
|---|---|---|
| oxiconazole nitrate | 1.147 | 11.47 |
| stearyl alcohol NF | 12.0 | 120 |
| cetyl alcohol NF | 4.5 | 45 |
| white petroleum USP | 15.0 | 150 |
| polysorbate 60 NF | 5.0 | 50 |
| propylene glycol USP | 11.5 | 115 |
| benzoic acid USP | 0.2 | 2 |
| purified water USP | 50.653 | 506.53 |

Excipient materials may vary ± 10%

EXAMPLE R

Oxiconazole 1% Lotion

| Ingredients | % w/w | For 1 gram (milligrams) |
|---|---|---|
| oxiconazole nitrate | 1.147 | 11.47 |
| stearyl alcohol NF | 4.0 | 40 |
| cetyl alcohol NF | 1.5 | 15 |
| white petrolatum USP | 5.0 | 50 |
| polysorbate 60 NF | 1.7 | 17 |
| propylene glycol USP | 3.8 | 38 |
| benzoic acid USP | 0.2 | 2 |
| purified water USP | 82.653 | 826.53 |

Excipient materials may vary ± 10%

What is claimed is:

1. A multiple dosage topical medicament container which comprises a first pharmaceutical composition comprising an effective amount of an antifungal agent and an antiinflammatory agent and a second pharmaceutical compositon consisting essentially of an effective amount of an anti-fungal agent wherein said medicament container is in the form of a dispenser having a single exit aperture for the first and second pharmaceutical compositions and means to effect delivery of the pharmaceutical compositions from the dispenser and wherein repeated activation of said means results in initial dispensing of only the first pharmaceutical composition and upon delivery of the desired amount thereof, dispensing of only the second pharmaceutical composition without adjusting the dispenser during delivery.

2. The medicament container of claim 1, wherein said anti-fungal agent in the first and second pharmaceutical compositions is the same.

3. The medicament container of claim 1, wherein said antiinflammatory agent is a steroid.

4. The medicament container of claim 1, wherein said anti-fungal agent is oxiconazole and said antiinflammatory agent is a steroid.

5. The medicament container of claim 1, wherein said antifungal agent is oxiconazole and said antiinflammatory agent is fluticasone.

6. The medicament container of claim 1, wherein said first and second pharmaceutical compositions are creams, ointments or lotions.

7. The medicament container of claim 1, further comprising means to keep the first and second pharmaceutical compositions out of physical contact with each other.

* * * * *